United States Patent
Sellinger et al.

(10) Patent No.: US 12,415,963 B2
(45) Date of Patent: Sep. 16, 2025

(54) HYDROGENATION OF ACETYLENES IN A HYDROCARBON STREAM

(71) Applicant: KELLOGG BROWN & ROOT LLC, Houston, TX (US)

(72) Inventors: David Sellinger, Houston, TX (US); Robert Choi, Houston, TX (US); Quo-Chen Yeh, Sugar Land, TX (US); Alok Srivastava, Houston, TX (US); Kristine E. Hamilton, Houston, TX (US); Michael A. Radzicki, Houston, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 18/736,236

(22) Filed: Jun. 6, 2024

(65) Prior Publication Data

US 2024/0318089 A1 Sep. 26, 2024

Related U.S. Application Data

(62) Division of application No. 17/729,975, filed on Apr. 26, 2022, now Pat. No. 12,037,553.

(60) Provisional application No. 63/180,296, filed on Apr. 27, 2021.

(51) Int. Cl.
*C10G 70/04* (2006.01)
*C10G 51/06* (2006.01)

(52) U.S. Cl.
CPC .......... *C10G 70/041* (2013.01); *C10G 51/06* (2013.01); *C10G 2300/1037* (2013.01); *C10G 2400/20* (2013.01)

(58) Field of Classification Search
CPC C10G 70/041; C10G 51/06; C10G 2300/103; C10G 2400/20; C07C 5/09; C07C 7/04; C07C 7/163; C07C 1/167
See application file for complete search history.

(56) References Cited

U.S. PATENT DOCUMENTS 6,420,619 B1 * 7/2002 Gartside ................. C07C 11/06
208/143

* cited by examiner

Primary Examiner — Thuan D Dang
(74) Attorney, Agent, or Firm — Gary M. Machetta

(57) ABSTRACT

A system for hydrogenation $C_3$ and $C_4$ acetylenes contained within a hydrocarbon stream generated in a stream cracker unit where a debutanizer is placed upstream of a depropanizer for more economical processing of the hydrocarbon stream to produce lighter hydrocarbons, where the system requires only one stripper tower downstream of hydrogenation to remove residual hydrogen.

4 Claims, 1 Drawing Sheet

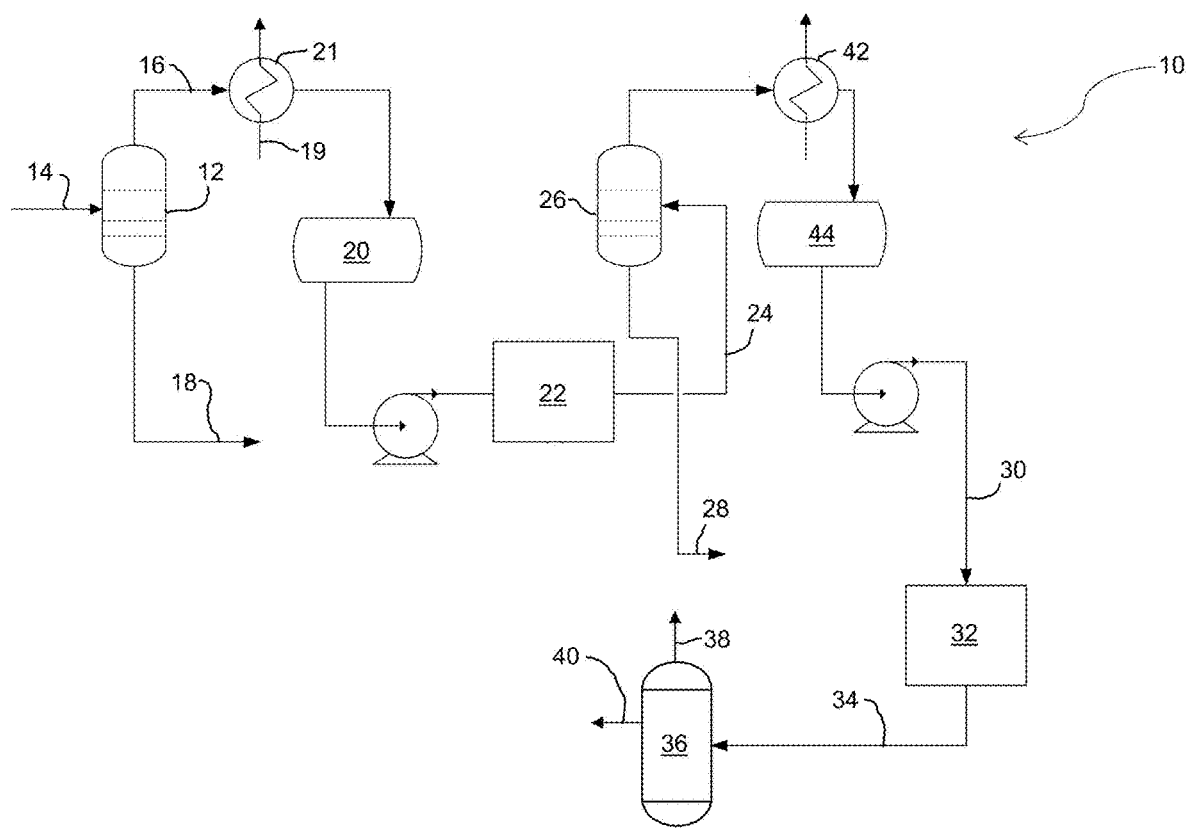

HYDROGENATION OF ACETYLENES IN A HYDROCARBON STREAM

CROSS REFERENCE TO RELATED APPLICATION

This application is a divisional of U.S. application Ser. No. 17/729,975, filed Apr. 26, 2022, which claims priority to U.S. Provisional Patent Application having Ser. No. 63/180,296 filed on Apr. 27, 2021, the contents of which are hereby incorporated by reference in its entirety.

TECHNICAL FIELD

The present invention relates to systems for hydrogenation of $C_4$ acetylenes, such vinyl and ethyl acetylenes, and $C_3$ acetylenes, such as methyl acetylene and propadiene, contained within a hydrocarbon stream being processed in a steam cracking process, and more particularly relates to such steam cracking processes required to meet product specifications on respective acetylenes.

BACKGROUND

In a conventional steam cracking process for the production of lighter hydrocarbons, a depropanizer, which separates a $C_3$ acetylene-rich hydrocarbon stream from $C_4$ acetylene-rich hydrocarbon stream, is placed upstream from a debutanizer. The $C_4$ acetylene-rich hydrocarbon stream leaving the depropanizer is sent to a debutanizer in which the $C_4$ acetylene-rich hydrocarbon is separated from the $C_5$-$C_{10}$ containing pyrolysis gas stream. The $C_4$ acetylene-rich hydrocarbon overhead of the debutanizer is then sent to a hydrogenation reactor in which it is hydrogenated over a selective catalyst. The $C_3$ acetylene-rich hydrocarbon overhead of the depropanizer is independently sent to a separate hydrogenation reactor to selectively hydrogenate the $C_3$ acetylene-rich hydrocarbon stream.

In this typical design, two separate stabilizing/stripper columns are required—one to vent off residual unreacted $H_2$ (hydrogen) from the $C_3$ hydrogenation reactor product stream and one to vent off residual unreacted $H_2$ (hydrogen) from the $C_4$ hydrogenation reactor product stream.

One prior process is seen in U.S. Pat. No. 5,090,977 to Exxon Chemical Patents Inc. that discloses a process sequence for treating cracked gases of heavy feedstocks which preferentially produces propylene to the exclusion of propane, butanes and butenes. The process eliminates the need for a depropanizer with the attendant savings in capital and operating costs. In lieu of a conventional C3 splitter, the process features a depropylenizer, i.e. a distillation tower designed to separate propylene from propane, butanes and butenes. A hydrogenation unit to eliminate contaminants can be placed upstream of the depropylenizer or the depropylenizer can be split into two sections with the hydrogenation unit located between the two sections.

Integration of gas oil and light olefin catalytic cracking zones with a pyrolytic cracking zone to maximize efficient production of petrochemicals is disclosed in U.S. Pat. No. 7,128,827 to Kellogg, Brown & Root LLC. Integration of the units in parallel allows production of an overall product stream with maximum ethylene and/or propylene by routing various feedstreams and recycle streams to the appropriate cracking zone(s), e.g. ethane/propane to the steam pyrolysis zone and $C_4$ $C_6$ olefins to the light olefin cracking zone. This integration enhances the value of the material balances produced by the integrated units.

Additionally, U.S. Pat. No. 7,294,749 to Kellogg, Brown & Root LLC describes a low-pressure olefins recovery process and plant. The feed gas 300 is compressed 302, 304 and distilled 310 at a primary distillation pressure. The overhead stream 312 is chilled 318 at a pressure less than 30 kg/cm$^2$ (430 psia) to partially condense the overheads. The primary distillation tower 310 is refluxed with at least a portion of the condensate 320. The overhead vapor is further chilled 318 and partially condensed and the condensate 322 is fed to a demethanizer 324. The remaining vapor 326 is cooled in a cold section 328 and the resultant liquid is phase-separated 330 and expanded 331, 334 to provide refrigeration for the cold section. The expanded vapor 332 from the cold section is recycled to the process gas compressor. The bottoms streams 338, 342 from the primary distillation zone and the demethanizer are fractionated into respective streams consisting essentially of ethylene 356, ethane 358, propylene 364, propane 366, $C_4$'s 346, and $C_{5+}$ 348.

However, there are significant capital and maintenance costs with building a steam cracking unit in which the system for hydrogenating acetylenes has this two stabilizing/stripper column design, which can create an economic barrier to building systems for oil and gas refining.

Thus, there is a need to lower capital costs associated with the production of lighter hydrocarbons and the hydrogenation of acetylenes in hydrocarbon streams, in particular.

SUMMARY

There is provided, in one non-limiting embodiment, a system for hydrogenating acetylenes in a hydrocarbon stream, the system including a depropanizer, a debutanizer, a $C_4$ acetylene hydrogenation reactor, a $C_3$ acetylene hydrogenation reactor, and a stripper column, where the depropanizer is located downstream of the debutanizer. In a different non-restrictive aspect, there is no stripping column additional to the stripper column for venting off residual unreacted $H_2$ from the crude butadiene stream.

In another non-limiting embodiment, there is provided a process for selective hydrogenation of acetylenes including directing a $C_3$-$C_{10}$ hydrocarbon stream to a debutanizer, selectively hydrogenating $C_4$ acetylenes in the condensed $C_3$-$C_4$ overhead stream in a $C_4$ acetylene hydrogenation reactor to give a reactor outlet stream, directing the reactor outlet stream to a depropanizer downstream from the debutanizer, drawing a top stream from the depropanizer containing a $C_3$ mixture comprising methyl acetylene and propadiene, drawing a bottom stream from the depropanizer containing a crude $C_4$ mixture, directing the $C_3$ mixture to a methyl acetylene and propadiene (MAPD) reactor and selectively hydrogenating the methyl acetylene and propadiene to give a crude propylene stream, and directing the crude propylene stream to a stripper column. In a different non-restrictive aspect, the stripper column is the only stripper column and there is an absence of a stripper column downstream of the $C_4$ acetylene hydrogenation reactor.

In a different non-limiting embodiment there is provided an ethylene plant including a system for hydrogenating acetylenes in a hydrocarbon stream, the system including a depropanizer, a debutanizer, a C4 acetylene hydrogenation reactor, a C3 acetylene hydrogenation reactor, and a stripper column, where the depropanizer is located downstream of the debutanizer. In a different non-restrictive aspect of the ethylene plant, there is no stripping column additional to the stripper column for venting off residual unreacted $H_2$ from the crude butadiene stream.

There is additionally provided an upgraded hydroprocessed product produced by the selective hydrogenation process herein that comprises from about 0.5 independently to about 2 wt % hydrogenated $C_4$ acetylenes; alternatively from about 0.9 independently to about 1.6 wt % hydrogenated $C_4$ acetylenes. Additionally, the upgraded hydroprocessed product has from about 20 wt % independently to about 60 wt % hydrogenated 1,3-butadiene; alternatively from about 40 independently to about 50 wt % hydrogenated 1,3-butadiene. The upgraded hydroprocessed product may also have from about 20 wt % independently to about 60 wt % of hydrogenated $C_3$ hydrocarbons; alternatively from about 40 wt % independently to about 50 wt % of hydrogenated $C_3$ hydrocarbons.

BRIEF DESCRIPTION OF THE DRAWINGS

FIG. 1 illustrates an example diagram of the system for hydrogenating acetylenes in a hydrocarbon stream as described herein.

DETAILED DESCRIPTION

It has been discovered that having a system for hydrogenating acetylenes in a stream cracker in which the debutanizer is located upstream from the depropanizer can eliminate the need for two separate stabilizing/stripping columns to vent off residual unreacted $H_2$ (hydrogen) present in the crude butadiene and crude propylene product streams. In other words, the present system and process switches the sequence of depropanizer and debutanizer where in debutanizer comes first and depropanizer is placed downstream of debutanizer. This is done because both $C_4$ acetylenes (vinyl acetylene, ethyl acetylene) and $C_3$ acetylenes (methyl acetylene, propadiene) need to be hydrogenated to meet crude butadiene and crude propylene product specifications on respective acetylenes. As noted, in the conventional sequence, this requires two separate stabilizing columns—one for crude butadiene and one for crude propylene to vent off the residual hydrogen unreacted in the hydrogenation reactor. These two separate columns add to the capital cost of the project. Thus, this system and process saves one tower which is significant cost saving.

A gas cracker typically includes an ethane feed (or a mix of ethane and propane) to a Pyrolysis System. The cracked gas passes to a Quench and Condensate Recovery System where it is cooled. The cooled crack gas feeds the Compression, Acid Gas Removal and Drying Systems. The compressed cracked gas feeds a Deethanizer and Acetylene Reactor Systems where the $C_2$ and lighter components are separated from the $C_3$ and heavier components. The $C_3$ and heavier components make up three products that have value: a propylene-rich mixed $C_3$s product, a crude butadiene product, and a pyrolysis gasoline product.

Producing the crude butadiene product normally would have the $C_3$ and heavier components feed a Depropanizer, with the bottoms then feeding a Debutanizer to produce a mixed $C_4$s product on the Debutanizer overhead. The Debutanizer overhead can then be treated in a $C_4$ Acetylene Reactor System provided to upgrade the crude butadiene product as the reduction or elimination of acetylenes can yield higher market value for the product stream or it could result in savings in a butadiene unit that exceed the cost of the $C_4$ Acetylene Reactor System. However the $C_4$ Acetylene Reactor System adds light end contaminants that would need to be removed by an additional Stripper System.

The hydrogenation of $C_3$ and $C_4$ acetylenes contained within a hydrocarbon stream being processed in a steam cracker unit stream may be accomplished, in one non-limiting embodiment, by the system shown in FIG. 1 and by the process described herein.

Referring to FIG. 1 and the overall system for hydrogenating acetylenes in a hydrocarbon stream 10, a debutanizer 12 receives a feed containing a mixture of $C_3$-$C_{10}$ range hydrocarbons 14. In one embodiment, the $C_4$ and $C_3$ hydrocarbons in the stream may be a mixture of saturates, olefins, diolefins, and acetylenes. Example feed conditions of the $C_4$ acetylenes and hydrogen ($H_2$) feed are provide in Table Y below along with operating conditions.

TABLE Y

| Feed conditions | | |
|---|---|---|
| Operating conditions | | |
| Pressure, kg/cm² (psia) | 24 (340) | |
| Temperature (inlet), F. (C.) | 93 (34) | |
| Feed, lb/hr (kg/hr) | 1 (0.45) | |
| H2, lb/hr (g/hr) | 0.0007 (0.318) | |
| Components | $C_4$ acetylenes reactor feed wt % | $H_2$ wt % |
| Hydrogen | 0.01 | 100 |
| Ethane | 0.04 | |
| Methyl Acetylene | 0.6 | |
| Propadiene | 0.4 | |
| Propylene | 41 | |
| Propane | 7 | |
| Vinyl Acetylene | 0.7 | |
| 1-Butyne | 0.1 | |
| 1,3-Butadiene | 38 | |
| 1-Butene | 4 | |
| Cis-2-Butene | 1 | |
| Trans-2-Butene | 1 | |
| Isobutylene | 0.2 | |
| n-Butane | 6 | |
| 3-Methyl-1-Butene | 0.1 | |
| Total | 100 | 100 |

The debutanizer overhead stream 16 is a mixture of $C_3$ and $C_4$ hydrocarbons, while the debutanizer bottoms stream 18 is a pyrolysis gasoline product stream containing $C_5$-$C_{10}$ hydrocarbons. It will be appreciated that the pressure and temperature of debutanizer 12 should be set in a manner in which the hydrocarbons in the debutanizer overhead stream 16 can be condensed using available economical refrigeration mediums. In one non-restrictive embodiment, the hydrocarbons are condensed at a pressure of about 50 psig (0.3 MPa). If condensed at this pressure, it will be appreciated that, since the debutanizer overhead stream 16 comprises a mixture of $C_3$ and $C_4$ hydrocarbons, a refrigeration medium 19 may be used in debutanizer condenser 21, and that the temperature of the debutanizer overhead stream 16 may be in the range of about 40-50° F. (about 4-10° C.) vs. conventional temperature of 100° F. (about 38° C.). The refrigeration medium 19 may a propylene stream from a steam cracker (not shown).

Continuing reference to FIG. 1, the debutanizer overhead stream 16, which is a mixture of $C_3$ and $C_4$ hydrocarbons in the form of saturates, olefins, and/or diolefins, after being directed through debutanizer reflux drum 20, is pumped to $C_4$ acetylene selective hydrogenation reactor 22 where $C_4$ acetylenes are selectively hydrogenated. In one non-limiting embodiment, the proportion of $C_3$ hydrocarbons in debutanizer overhead stream 16 is at least 20 wt % $C_3$ hydrocarbons and $C_4$ hydrocarbons including $C_4$ acetylenes and 1,3-butadiene. A molecular hydrogen-containing stream (not shown) introduced prior to the $C_4$ acetylene selective hydrogenation reactor 22 may have at least 35 wt % molecular hydrogen, alternatively at least 99 wt % molecular hydrogen, and in another non-limiting version may be substantially pure molecular hydrogen.

The temperature at the $C_4$ acetylene selective hydrogenation reactor 22 inlet is in a range of from about 50° F. (10° C.) independently to about 140° F. (about 60° C.) from start of run to end of run, alternatively from about 78° F. (25° C.) independently to about 95° F. (35° C.). As used herein with respect to a parameter range, the word "independently" means that any range endpoint may be used together with any other range endpoint to give an acceptable alternative range.

The $C_3$ and $C_4$ hydrocarbons should be around 99 percent in liquid phase. The $C_3$ and $C_4$ vaporization is not used to control the reactor temperature. The reactor 22's total pressure is at least that needed to maintain the $C_3$ and $C_4$ hydrocarbons in the liquid phase during the hydrogenation. In one non-limiting embodiment the pressure ranges from about 300 psia (about 2.1 MPa) independently to about 600 psia (about 4.9 MPa); alternatively from about 350 psia (about 2.5 MPa) independently to about 400 psia (2.8 MPa). Higher pressure is better for hydrogen solubility in feed and should be high enough to keep hydrocarbons in liquid phase through the $C_4$ acetylene selective hydrogenation reactor 22.

In one embodiment, the $C_4$ acetylene converter outlet components are:

| Components | C4 acetylene converter outlet wt % |
|---|---|
| Hydrogen | 0.01 |
| Methane | 0.00 |
| Ethane | 0.04 |
| Methyl Acetylene | 0 |
| Propadiene | 0 |
| Propylene | 41 |
| Propane | 7 |
| Vinyl Acetylene | 0 |
| 1-Butyne | 0 |
| 1,3-Butadiene | 37 |
| 1-Butene | 5 |
| Cis-2-Butene | 1 |
| Trans-2-Butene | 1 |
| Isobutylene | 0 |
| n-Butane | 6 |
| Cyclopentadiene | 0 |
| 2-Mehtyl-1,3-Butadiene | 0 |
| Total | 100 |

Selective hydrogenation is carried out by controlled injection of $H_2$ to hydrogenate $C_4$ acetylenes selectively on a catalyst fixed bed. Unreacted $H_2$ from effluent of reactor is sent to cracked gas compressor suction after cooling and separating in a separator drum The upgraded $C_3$ and $C_4$ outlet stream 24 of the $C_4$ acetylene selective hydrogenation reactor 22 is sent to a depropanizer 26, which separates a bottoms crude butadiene product stream 28 from net depropanizer overhead stream 30. The depropanizer bottoms stream is the bottoms crude butadiene product stream 28, while the net depropanizer overhead stream 30 is a mixture of $C_3$ hydrocarbons, the latter which is passed through depropanizer condenser 42. The net depropanizer overhead stream 30 is then pumped from depropanizer reflux drum 44 to MAPD (methyl acetylene and propadiene) reactor 32 to selectively hydrogenate $C_3$ acetylenes, such as, without limitation, methyl acetylene and propadiene. After selective hydrogenation of $C_3$ acetylenes in the MAPD reactor 32, the upgraded mixed $C_3$ hydrocarbon stream 34 leaving the MAPD reactor 32 goes to a $C_3$ stripper column 36 where unreacted $H_2$ and lights 38 (typically comprising methane and trace $C_2$s) are vented out and propylene product 40 is withdrawn, in one form, as a side draw from the $C_3$ stripper column 36. In this non-limiting embodiment, it is appreciated that because the depropanizer 26 functions to separate lighter hydrocarbons from $C_4$ hydrocarbons in the stream, it is not necessary for the crude butadiene product stream 28 leaving the bottom of the depropanizer 26 to be sent to a separate stripping column to vent off residual unreacted $H_2$.

In one non-limiting embodiment, the hydrocarbons in the stream, feed containing a mixture of $C_3$-$C_{10}$ range hydrocarbons 14, may be a mixture of saturates, olefins, and acetylenes.

The hydrogenation catalyst(s) useful for selectively hydrogenating the $C_4$ acetylenes in the stream may include, but are not necessarily limited to, palladium-based catalysts, such as; palladium-on-alumina, copper-based catalysts, rhodium-based catalysts, and other such metal based catalysts. The hydrogenation catalyst(s) useful for selectively hydrogenating the $C_3$ acetylenes in the stream may include, but are not necessarily limited to, palladium-based catalysts, such as; palladium-on-alumina, copper-based catalysts, rhodium-based catalysts, and other such metal based catalysts.

It is appreciated that conversion of $C_4$ acetylenes can be targeted to meet the specifications for $C_4$ acetylenes in the product crude butadiene stream. This is accomplished by controlled injection of $H_2$ to hydrogenate $C_4$ acetylenes selectively. The reactor size, recycle rate, pressure, and temperature of reactor inlet may be designed to achieve or exceed the desired conversion of $C_4$ acetylenes and to decease or even minimize conversion of the 1,3-butadiene and propylene present in the crude butadiene stream. In one exemplary embodiment, the desired run length may be in the range of about 2 months independently to about 12 months; alternatively from about 6 independently to about 9 months; and the range of space velocity (LHSV) may be in the range of 4 independently to about 20; alternatively from about 8 independently to about 16.

It will also be appreciated that any hydrogenation of $C_3$ acetylenes, such as methyl acetylene and propadiene, in this process, though not intended, is beneficial.

The processes and systems described herein may accomplish a variety of goals including, but not necessarily limited to:

hydrogenating $C_4$ acetylenes in mixed hydrocarbon streams in a manner that substantially maintains selectively and conversion for hydrogenating the $C_4$ acetylenes;

hydrogenating $C_4$ acetylenes in mixed hydrocarbon streams in a manner that gives increased selectivity and/or conversion; and hydrogenating $C_4$ acetylenes in mixed hydrocarbon streams with decreased hydrogenation of valuable hydrocarbons such as 1,3-butadiene and propylene.

The processes and systems described herein are considered effective and successful even if only one of these goals is accomplished, such as achieving substantially the selectivity and conversion of $C_4$ acetylenes in a mixed $C_3/C_4$ stream with a $C_4$ stream. The processes and systems may be considered even more effective if one or more of the other goals is/are also achieved.

In the foregoing specification, the invention has been described with reference to specific embodiments thereof. However, the specification is to be regarded in an illustrative rather than a restrictive sense. For example, hydrogenation reaction conditions and equipment, debutanizer and depropanizer conditions, catalysts, and composition and conditions of hydrocarbon and acetylene streams, hydrogen streams, falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. For instance, the system may comprise, consist of, or consist essentially of: a depropanizer, a debutanizer, a $C_4$ acetylene-rich hydrogenation reactor, a methyl acetylene and propadiene (MAPD) reactor, and a stripper column, where the depropanizer is located downstream of the debutanizer.

In another non-limiting embodiment there may be provided a process for selective hydrogenation of acetylenes comprising, consisting essentially of, or consisting of directing a $C_3$-$C_{10}$ hydrocarbon stream to a debutanizer, condensing a debutanizer $C_3$-$C_4$ overhead stream, selectively hydrogenating $C_4$ acetylenes in the condensed $C_3$-$C_4$ overhead stream in a $C_4$ acetylene hydrogenation reactor to give a reactor outlet stream, directing the reactor outlet stream to a depropanizer downstream from the debutanizer, drawing a top stream from the depropanizer containing a $C_3$ mixture comprising methyl acetylene and propadiene, drawing a bottom stream from the depropanizer containing a crude $C_4$ mixture, directing the $C_3$ mixture to a methyl acetylene and propadiene (MAPD) reactor and selectively hydrogenating the methyl acetylene and propadiene to give a crude propylene stream, and directing the crude propylene stream to a stripper column.

Additionally, there may be provided an upgraded hydroprocessed product produced by the selective hydrogenation process herein that comprises from about 0.5 independently to about 2 wt % hydrogenated $C_4$ acetylenes; alternatively from about 0.9 independently to about 1.6 wt % hydrogenated $C_4$ acetylenes. Additionally, the upgraded hydroprocessed product has from about 20 wt % independently to about 60 wt % hydrogenated 1,3-butadiene; alternatively from about 40 independently to about 50 wt % hydrogenated 1,3-butadiene.

Furthermore there may be provided in another non-limiting embodiment an ethylene plant comprising, consisting essentially of, or consisting of a system for hydrogenating acetylenes in a hydrocarbon stream, the system comprising, consisting essentially of, or consisting of, a depropanizer, a debutanizer, a $C_4$ acetylene hydrogenation reactor, a methyl acetylene and propadiene (MAPD) reactor, and a stripper column, where the depropanizer is located downstream of the debutanizer.

The words "comprising" and "comprises" as used throughout the claims, are to be interpreted to mean "including but not limited to" and "includes but not limited to", respectively.

To the extent used herein, the word "substantially" shall mean "being largely but not wholly that which is specified."

As used herein, the singular forms "a," "an," and "the" are intended to include the plural forms as well, unless the context clearly indicates otherwise.

To the extent used herein, the term "about" in reference to a given parameter is inclusive of the stated value and has the meaning dictated by the context (e.g., it includes the degree of error associated with measurement of the given parameter).

To the extent used herein, the term "and/or" includes any and all combinations of one or more of the associated listed items.

What is claimed is:

1. A process for selective hydrogenation of acetylenes comprising:
    directing a $C_3$-$C_{10}$ hydrocarbon stream to a debutanizer;
    condensing a debutanizer $C_3$-$C_4$ overhead stream;
    selectively hydrogenating $C_4$ acetylenes in the condensed $C_3$-$C_4$ overhead stream in a $C_4$ acetylene hydrogenation reactor to give a reactor outlet stream;
    directing the reactor outlet stream to a depropanizer downstream from the debutanizer;
    drawing a top stream from the depropanizer containing a $C_3$ mixture comprising methyl acetylene and propadiene;
    drawing a bottom stream from the depropanizer containing a crude $C_4$ mixture;
    directing the $C_3$ mixture to a methyl acetylene and propadiene (MAPD) reactor and selectively hydrogenating the methyl acetylene and propadiene to give a crude propylene stream; and
    directing the crude propylene stream to a stripper column to vent off residual unreacted hydrogen.

2. The process of claim 1 where the stripper column is the only stripper column and in the absence of a stripper column downstream of the crude $C_4$ mixture.

3. The process of claim 1 where condensing a debutanizer $C_3$-$C_4$ overhead stream is conducted against a refrigeration medium.

4. The process of claim 1 where the $C_4$ acetylene hydrogenation reactor is operated at a temperature of from about 50° F. (10° C.) to about 140° F. (about 60° C.), and a pressure of from about 300 psia (about 2.1 MPa) to about 600 psia (about 4.9 MPa).

* * * * *